(12) United States Patent
Schröder et al.

(10) Patent No.: US 6,498,272 B1
(45) Date of Patent: Dec. 24, 2002

(54) METHOD FOR PRODUCING ACRYLIC ACID

(75) Inventors: Jürgen Schröder; Gerhard Nestler, both of Ludwigshafen; Klaus Joachim Müller-Engel, Stutensee, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/914,533

(22) PCT Filed: Feb. 28, 2000

(86) PCT No.: PCT/EP00/01635

§ 371 (c)(1),
(2), (4) Date: Aug. 30, 2001

(87) PCT Pub. No.: WO00/53560

PCT Pub. Date: Sep. 14, 2000

(30) Foreign Application Priority Data

Mar. 6, 1999 (DE) .......................... 199 09 923
May 28, 1999 (DE) .......................... 199 24 533

(51) Int. Cl.$^7$ .......................... C07C 51/42; C07C 27/10
(52) U.S. Cl. .................... 562/600; 562/598; 562/512.2
(58) Field of Search ................ 562/598, 600, 562/512.2

(56) References Cited

U.S. PATENT DOCUMENTS

| | | |
|---|---|---|
| 2,806,878 A | 9/1957 | Luberoff |
| 3,086,046 A | 4/1963 | Von Kutepow et al. |
| 3,639,466 A | 2/1972 | Leichtle |
| 3,932,500 A | 1/1976 | Duembgen et al. |
| 4,317,926 A | 3/1982 | Sato et al. |
| 5,087,744 A | 2/1992 | Krabetz et al. |
| 5,734,075 A | 3/1998 | Fauconet et al. |
| 5,910,603 A | 6/1999 | Aichinger et al. |

FOREIGN PATENT DOCUMENTS

| | | |
|---|---|---|
| DE | 21 36 396 | 2/1973 |
| DE | 16 18 129 | 7/1976 |
| DE | 29 01 783 | 8/1979 |
| DE | 41 01 879 | 7/1992 |
| DE | 195 36 191 | 4/1997 |
| DE | 197 01 737 | 7/1998 |
| DE | 197 40 252 | 3/1999 |
| DE | 197 40 253 | 3/1999 |
| DE | 198 14 375 | 10/1999 |
| DE | 198 14 387 | 10/1999 |
| DE | 198 14 421 | 10/1999 |
| DE | 199 09 923 | 3/2000 |
| EP | 0 297 445 | 1/1989 |
| EP | 0 717 031 | 6/1996 |
| WO | WO 99/50219 | * 3/1999 |
| WO | WO99/50219 | 10/1999 |
| WO | WO 99/50220 | 10/1999 |

OTHER PUBLICATIONS

Ullmanns Encyclopaedie der Technischen Chemie, vol. 7, p. 83 and p. 93, "Acrylsaeure".

W. Gerharz, et al., Ullmann's Encyclopedia of Industrial Chemistry, vol. A1, pp. 166–167, "Acrylic Acid and Derivatives".

* cited by examiner

Primary Examiner—Johann Richter
Assistant Examiner—Farhad Forohar
(74) Attorney, Agent, or Firm—Oblon, Spivak, McClelland, Maier & Neustadt, P.C.

(57) ABSTRACT

In a process for the preparation of acrylic acid, a product gas mixture obtained by catalytic gas-phase oxidation of a $C_3$-precursor of acrylic acid and containing acrylic acid is directly cooled with a quench liquid and then subjected to fractional condensation in a separation column provided with baffles, said product gas mixture ascending into itself and a crude acrylic acid being removed via a side take-off, and the acrylic acid oligomers formed are cleaved and recycled.

12 Claims, 2 Drawing Sheets

METHOD FOR PRODUCING ACRYLIC ACID

The present invention relates to a process for the preparation of acrylic acid, in which an acrylic acid-containing hot product gas mixture is produced by gas-phase partial oxidation of propane or propene and/or acrolein with molecular oxygen under heterogeneous catalysis over catalysts present in the solid state at elevated temperature, the temperature of the hot acrylic acid-containing product gas mixture is reduced by means of a quench liquid, the unvaporized part of the quench liquid 1 is circulated, if required via a heat exchanger providing indirect cooling, and a part of the unvaporized quench liquid 1 is removed as a purge from the circulation, and the cooled product gas mixture is then passed into a column equipped with baffles having separation activity, allowed to ascend into itself inside the column and subjected to fractional condensation, a crude acrylic acid being removed at the side take-off and bottom liquid containing acrylic acid oligomers and/or a high boiler fraction being removed via the bottom of the column and/or via a side take-off in the vicinity of the bottom and being used as quench liquid 1.

Acrylic acid is an important intermediate which is used, for example, in the preparation of polymer dispersions.

Acrylic acid is obtainable, inter alia, by gas-phase partial oxidation of propane or propene and/or acrolein with molecular oxygen under heterogeneous catalysis over catalysts present in the solid state, at elevated temperatures. Said starting gases, as a rule diluted with inert gases, such as nitrogen, $CO_2$ and/or steam, are passed as a mixture with molecular oxygen, at elevated temperature and, if required, superatmospheric pressure, over transition metal mixed oxide catalysts and are converted by oxidation into an acrylic acid-containing product gas mixture.

By absorption into a suitable absorbent, for example water, or a mixture of from 70 to 75% by weight of diphenyl ether and from 25 to 30% by weight of biphenyl, a basic separation of the acrylic acid from the product gas stream can be achieved, (c.f. for example EP-A 297445 and DE-C 2136396).

Removing the absorbent by means of distillative separation methods usually gives an acrylic acid which is not yet a pure product and is therefore usually referred to as crude acrylic acid, which can be further purified in various ways.

However, the disadvantage of the abovementioned distillative separation method is that, in spite of the presence of free radical polymerization inhibitors, they give rise to the formation of such a large amount of acrylic acid which has undergone free radical polymerization in an undesired manner that the distillation apparatus has to be switched off periodically (as a rule every few weeks) to remove the polymer.

DE-A 19740253, DE-A 19740252, DE-A 19814421, 19814387 and 19814375 disclose a process, as described at the outset, for the preparation of acrylic acid, in which the basic isolation of the crude acrylic acid is carried out by fractional condensation of the product gas mixture of the gas-phase partial oxidation under heterogeneous catalysis. Such a procedure is also the subject of DE-A 19909923.

Surprisingly and incomprehensibly, it has been found that a major advantage of the abovementioned basic isolation of crude acrylic acid by fractional condensation is that, in the presence of free radical polymerization inhibitors, it is disturbed only to a substantially reduced extent by the formation of acrylic acid which has undergone free radical polymerization.

However, the disadvantage is still that acrylic acid in the condensed phase forms acrylic acid oligomers (Michael adducts) by Michael addition with itself and with the acrylic acid dimers forming (in this publication, the term acrylic acid oligomers always means the corresponding Michael adducts and not acrylic oligomers formed by free radical polymerization). The presence of water, the unavoidable by-product of gas-phase catalytic oxidative preparation of acrylic acid, at elevated temperature promotes the formation of acrylic acid oligomers.

Since acrylic acid oligomers have a higher boiling point than acrylic acid, they accumulate in the bottom liquid both during the distillative isolation of acrylic acid and in a fraction condensation of the product gas mixture of gas-phase catalytic oxidative acrylic acid production.

In principle, the formation of acrylic acid oligomers is undesirable since they reduce the yield of the desired product.

It is generally known that the formation of acrylic acid oligomers is a reversible process which can be reversed by the action of elevated temperatures (cf. for example, DE-A 4101879, DE-A 19701737, DE-A 19536191, U.S. Pat. No. 5,734,075, DE-A 2901783, U.S. Pat. Nos. 3,086,046, 2,806,878, German Patent 1618129, Ullmanns Encyclopädie der technischen Chemie, 4th Edition, Volume 7, Verlag Chemie, Weinheim, page 83, right column, and Ullmann's Encyclopedia of Industrial Chemistry, Fifth, Completely Revised Edition, Verlag Chemie, Weinheim, Vol. A11, page 167, right column).

This thermal cleavage can be carried out under both acidic and basic catalysis or in the absence of catalysts (cf. for example, EP-A 717031).

It is an object of the present invention to integrate, into the process, as described at the outset, for the preparation of acrylic acid, in which the basic isolation of the crude acrylic acid is carried out by fractional condensation of the product gas mixture of the gas-phase partial oxidation under heterogeneous catalysis, a cleavage of the acrylic acid oligomers contained in the purge of quench liquid 1, so that the runtime of the process, in particular that of the column for the fractional condensation, is essentially not reduced.

We have found that this object is achieved by a process for the preparation of acrylic acid, in which an acrylic acid-containing hot product gas mixture is produced by gas-phase partial oxidation of propane or propene and/or acrolein with molecular oxygen under heterogeneous catalysis over catalysts present in the solid state at elevated temperature, the temperature of the hot acrylic acid-containing product gas mixture is reduced by direct cooling by means of a quench liquid 1, the unvaporized part of the quench liquid 1 is circulated, if required via a heat exchanger providing indirect cooling, and a part of the unvaporized quench liquid 1 is removed as a purge from the circulation, and the cooled product gas mixture is then passed into a column equipped with baffles having separation activity, allowed to ascend into itself inside the column and subjected to fractional condensation, a crude acrylic acid being removed at the side take-off and bottom liquid containing acrylic acid oligomers and/or a high boiler fraction (more sparingly volatile than acrylic acid) being removed via the bottom of the column and/or via a side take-off in the vicinity of the bottom and being used as quench liquid 1, wherein the purged quench liquid 1 is fed to a cleavage vessel, the acrylic acid oligomers contained in the purged quench liquid 1 are cleaved in said vessel at elevated temperatures to give acrylic acid, acrylic acid escaping in gaseous form from the liquid phase is condensed and the resulting condensate is fed into the circulation of the quench liquid 1.

The point of introduction of the quenched product gas mixture of the catalytic gas-phase oxidation into the column equipped with baffles having separation activity is expediently located below said baffles. In principle, fractional condensation can be carried out inside the column in a manner known per se by indirect cooling and/or heating. However, it is more expedient to effect the fractional condensation as follows. A part of the substances that form and/or condense as the quenched product gas mixture ascends and which have a higher boiling point than acrylic acid is removed via a first collecting tray mounted above the introduction point and below the baffles. A part of the high-boiler fraction removed is used as quench liquid 1 in the form of a mixture with the bottom liquid removed from the column and the remaining portion of the high-boiler fraction removed is cooled or heated in an indirect heat exchanger and recycled to the column above the first collecting tray but below a second collecting tray mounted in the lower half of the column. The crude acrylic acid, which usually has a purity ≧95% by weight, is removed via the second collecting tray, at a side take-off, as a medium-boiler friction. Expediently, the crude acrylic acid is fed to further purification stages involving distillation and/or crystallization, and at least a part of the bottom liquids and/or mother liquors obtained in the distillations and/or crystallizations is recycled to the column below the second but above the first collecting tray. Alternatively, the recycling of the bottom liquids and/or mother liquors may also be carried out by dividing them into two part-streams, one of which is recycled to the column below the second but above the first collecting tray and the other is recycled to said column above the second collecting tray. The last-mentioned of the two part-streams comprises as a rule up to 35% by weight, based on the total recycled material. Essentially water and components more sparingly volatile than water are condensed from the low-boiler gas stream escaping at the top of the column, expediently by direct cooling in a space free of baffles or containing baffles, by means of a second quench liquid (in this publication, referred to as quench liquid 2 for differentiation). The condensate obtained is referred to as dilute acid solution. The part of the dilute acid solution is usually recycled to the column to increase the separation efficiency at the top of said column. A further part of the dilute acid solution is expediently removed and disposed of (for example incinerated) and the remaining part of the dilute acid solution is usually indirectly cooled in an external heat exchanger and used as quench liquid 2.

Those components of the low-boiler stream which are more readily volatile than water are essentially taken off in gaseous form and, if required, recycled as diluent gas to the gas-phase oxidation.

Alternatively, the quench using the dilute acid solution can be integrated into the column for the fractional condensation. In this case, aqueous reflux liquid is removed via a further collecting tray in the upper part of the column, cooled indirectly in a heat exchanger and, apart from the purge to be disposed of, recycled partly to the top of the column and partly below the collecting tray. Any exit gas to be recycled to the gas-phase oxidation leaves the column in this case at its top.

The quenching of the product gas mixture of the gas-phase partial oxidation under heterogeneous catalysis with the quench liquid 1 is carried out as a rule in a space free of baffles. The quench liquid 1 thereby reaching the cooling limit temperature is recycled, if necessary via an external heat exchanger, and reused for direct cooling. A part of the quench liquid 1 is removed from the circulation as a purge and is fed to the cleavage to be integrated according to the invention.

The purity of the crude acrylic acid removed from the fractional condensation column via a side take-off is usually ≧95% by weight, i.e. the crude acrylic acid contains at least 95%, based on its weight, of acrylic acid molecules.

The inhibition of polymerization in the novel process can be carried out essentially as described in DE-A 19909923, i.e. it can be effected, for example, by adding, at the top of the condensation column, phenothiazine or a mixture of an N-oxyl radical and a benzene compound which has two substituents bonded to the aromatic ring via heteroatoms and at least one mobile hydrogen.

In a more advantageous form of the inhibition of polymerization, said inhibition is carried out exclusively by means of N-oxyl radicals (for example those stated in EP-A 765856). These compound which have at least one —N—O.group.

N-oxyl radicals preferred according to the invention are the pyrrolidin-1-oxyl types and the piperidin-1-oxyl type. Examples are 4,4',4"-tris-(2,2,6,6-tetramethylpiperidin-1-oxyl)phosphite, 2,2,6,6-tetramethylpiperidin-1-oxyl (TEMPO), 4-hydroxy-2,2,6,6-tetramethylpiperidin-1-oxyl (4-OH-TEMPO), 4-oxo-2,2,6,6-tetramethylpiperidin-1-oxyl (4-oxo-TEMPO), 4-dimethylamino-2,2,6,6-tetramethylpiperidin-1-oxyl, 4-amino-2,2,6,6-tetramethylpiperidin-1-oxyl, 4-ethanoyloxy-2,2,6,6-tetramethylpiperidin-1-oxyl, 2,2,5,5-tetramethylpyrrolidin-1-oxyl and 3-amino-2,2,5,5-tetramethylpyrrolidin-1-oxyl. The N-oxyl inhibitors are preferably used as from 0.1 to 2% strength by weight solutions in water and/or in dilute acid solution. Addition of the aqueous N-oxyl inhibitor solution is expediently effected in the upper fourth of the condensation column and/or in the quench using dilute acid solution. The aqueous solution contain only one N-oxyl radical or a mixture of N-oxyl radicals. Adequate inhibition can be achieved by adding an aqueous solution which contains exclusively 4-OH-TEMPO as a polymerization inhibitor.

The added amount of the N-oxyl inhibitors to be used is expediently such that the bottom liquid and high-boiler fraction removed from the column contains from 1 to 1000 ppm by weight, based on the weight of the high-boiler fraction, of N-oxyl inhibitors. Since the bottom liquid and high-boiler fraction removed from the column is used as quench liquid 1, the quench system 1 is automatically costabilized. If required, the quench system 1 can be costabilized by adding a phenothiazine compound. Suitable phenothiazine compounds of this type are, for example, phenothiazine (PTZ) itself, bis(α-methylbenzyl) phenothiazine, 3,7-dioctylphenothiazine and bis(α-dimethylbenzyl)phenothiazine, among which phenothiazine is preferred. The latter applies particularly when 4-OH-TEMPO is used concomitantly or exclusively for stabilizing the condensation column. Such a phenothiazine addition may amount to from 1 to 500 ppm by weight, based on the weight of the quench liquid. Expediently, such an addition of a phenothiazine compound is effected in solution in acrylic acid, preferably in solution in crude acrylic acid removed via a side take-off (typically from 0.1 to 2% strength by weight). The amount of N-oxyl radicals required for inhibiting polymerization can be reduced by carrying out the less demanding stabilization of dilute acid solution, i.e. the stabilization of the quench system 2, alternatively or in combination with an aqueous solution of at least one benzene compound which has two substituents bonded to the aromatic ring via hetero atoms and at least one mobile hydrogen (for example those stated in EP-A 766856), for example a phenol compound (typically from 0.1 to 2% strength by weight solution). Suitable phenol compounds of this type are, for example, hydroquinone and methoquinone (p-methoxyphenol=MEHQ), among which the latter is preferred. This applies in particular when exclusively 4-OH-TEMPO is used in the top region of the column and the quench system is costabilized with PTZ. As a rule, from 1 to 500 ppm by weight, based on the weight of the dilute acid solution, of at least one phenol compound are used for such inhibition of dilute acid solutions.

An alternative inhibition of polymerization comprises adding an aqueous solution of MEHQ at the top of the condensation column and carrying out the inhibition of the dilute acid solution likewise by adding a solution of MEHQ in water and/or in dilute acid solution. In addition, a solution of PTZ in acrylic acid (e.g. crude acrylic acid) is added in the middle part of the condensation column and, if required, in the product gas mixture quench (quench 1).

As stated above, the quench system 1 is automatically costabilized by means of the stabilization of the condensation column and can, if required, be costabilized by adding phenothiazine and/or methoquinone.

The resulting inhibition of polymerization of the quench liquid 1 is as a rule also sufficient to ensure sufficient stability of the purge quench liquid 1 to undesired polymer formation during the cleavage to be integrated according to the invention. On the other hand, in the condensation of the vapor escaping in gaseous form during the cleavage and containing acrylic acid, the condenser surfaces are expediently additionally inhibited (the inhibitors contained in the quench liquid 1 do not as a rule also vaporize). This inhibition of polymerization of the condenser surfaces is advantageously carried out using the same polymerization inhibitors as those also used and/or recommended for inhibition of the condensation column. If, for example, exclusively 4-OH-TEMPO is used for stabilization of the condensation column and the quench with dilute acid solution, it is useful to stabilize the condenser surfaces also exclusively with 4-OH-TEMPO, expediently dissolved in crude acrylic acid. However, the condenser surfaces can of course also be costabilized or exclusively stabilized by means of PTZ, MEHQ and/or hydroquinone.

As a rule, the cleavage to be integrated according to the invention is carried out at $\leq 1$ bar and at from 130 to 250° C. Advantageously, the pressure for the cleavage is from 25 to 600 mbar, preferably from 100 to 300 mbar. The cleavage temperature is expediently from 140 to 230° C., preferably from 160 to 200° C. If the cleavage is carried out continuously (the novel process is preferably carried out continuously), the residence time in the cleavage reactor should be from about 0.5 to 3 hours. The cleavage to be integrated according to the invention can be carried out in a simple manner in a heatable stirred reactor. 0050/50009

As described in U.S. Pat. No. 5,734,075 and DE-A 4101879, the cleavage of the acrylic acid oligomers contained in the purged quench system 1 can be carried out without the addition of special acidic or basic cleavage catalysts. Advantageously, however, the cleavage is carried out in the presence of cleavage catalysts. Suitable cleavage catalysts are, for example, dodecylbenzenesulfonic acid, p-toluenesulfonic acid, sulfuric acid or the solid acidic catalysts of JP-A 3-178949.

Particularly where polymerization is inhibited by means of N-oxyl radicals, especially when 4-OH-TEMPO is used as the sole polymerization inhibitor or as a costabilizer of the quench system 1, it is expedient to carry out the cleavage by adding an inorganic salt, the addition of which to an aqueous solution of a strong Brönsted acid shifts the pH of the aqueous solution towards the alkaline, as recommended, for example in DE-C 2407236. The amount of basic cleavage catalyst to be added is as a rule from 0.1 to 5% by weight, based on the amount of purged quench liquid 1 to be subjected to the cleavage. Examples of cleavage catalysts suitable according to the invention are KOH, $K_2CO_3$, $KHCO_3$, NaOH, $Na_2CO_3$, $NaHCO_3$, LiOH, $Li_2CO_3$ and $CaCO_3$.

This means that suitable cleavage catalysts are in particular the alkali metal and/or alkaline earth metal salts of weak, inorganic or organic Brönsted acids, e.g. phosphoric acid, boric acid, carbonic acid, formic acid or acetic acid. In other words, particularly suitable cleavage catalysts are therefore alkali metal and/or alkaline earth metal phosphates, borates, carbonates, bicarbonates, formates and acetates.

Preferably, the cleavage catalysts are chosen so that they are soluble in the purged quench liquid 1 under the cleavage conditions. According to U.S. Pat. No. 4,293,347, the presence of dialkyl phthalates also has an advantageous effect on the relevant cleavage.

The sparingly volatile residue remaining in the cleavage reactor is regularly disposed, for example incinerated, in the novel process. For this purpose, the cleavage residue can if required be diluted with hydrophilic organic liquids such as organic acids (e.g. ethylhexanoic acid, propionic acid) or residues from the preparation of these acids but also with alkanols such as ethanol or methanol.

At this point, it should also be stated that an inert organic liquid which has a higher boiling point than acrylic acid and keeps the quench liquid 1 fluid can, if required, be added to the quench liquid 1 to be used in the novel process.

Suitable high-boiling inert organic liquids of this type are in particular all those which are recommended in DE-A 2136396 and in DE-A 4308087. These are essentially liquids whose boiling point at atmospheric pressure is above 160° C. Examples are ethylhexanoic acid, N-methypyrrolidone, middle oil fractions from paraffin distillation, diphenyl ether, biphenyl or mixtures of the abovementioned liquids, for example a mixture of from 70 to 75% by weight of diphenyl ether and from 25 to 30% by weight of biphenyl. The use of a mixture consisting of from 70 to 75% by weight of diphenyl ether and from 25 to 30% by weight of diphenyl and, based on this mixture, from 0.1 to 25% by weight of dimethyl phthalate is advantageous.

In the abovementioned case, at least a portion of the inert organic liquid present is co-vaporized during the cleavage. If a portion of the organic liquid remains in the cleavage residue, the latter can be worked up by a procedure in which the solvent present is separated off, for example by distillation, and is recycled to the quench 1. The remaining high boilers are disposed of.

Frequently, the hot product gas mixtures of the gas-phase oxidation under heterogeneous catalysis have the following composition:

from 1 to 30% by weight of acrylic acid,
from 0.01 to 3% by weight of acetic acid, from 0.01 to 1% by weight of propionic acid, from 0.01 to 0.5% by weight of maleic acid/maleic anhydride, from 0.05 to 1% by weight of acrolein, from 0.05 to 1% by weight of formaldehyde, from 0.1 to 1% by weight of furfural, from 0.01 to 0.5% by weight of benzaldehyde, from 0.01 to 1% by weight of propene, from 0.05 to 10% by weight of oxygen, and from 1 to 30% by weight of water and the remaining amount comprising inert gases, e.g. nitrogen, carbon oxides, methane and propane.

The gas-phase oxidation itself can be carried out, for example, in two successive oxidation stages, as described in EP-A 700 714 and in EP-A 700 893. However, the gas-phase oxidation cited in DE-A 19740253 and in DE-A 19740252 can of course also be used.

As a rule, the temperature of the product gas mixture leaving the gas-phase oxidation is from 150 to 350° C., in general from 200 to 300° C. In the quench system 1, the hot product gas mixture is usually cooled to a temperature of from 100 to 180° C., at which it is then fed to the lowermost section of the separation column. The operating pressure prevailing in the column is as a rule from 0.5 to 5, frequently from 5 to 3, in many cases from 0.5 to 2, bar.

The quench apparatus 1 used may be any apparatus known in the prior art for this purpose (for example, spray scrubbers, Venturi scrubbers, bubble columns or other apparatuses having sprayed surfaces), according to the invention Venturi scrubbers or spray coolers preferably being used.

All conventional heat exchangers are suitable for the indirect cooling or heating of the quench liquid 1. Tube-bundle heat exchangers, plate-type heat exchangers and air coolers may be mentioned as being preferred. The temperature of the quench liquid 1 after leaving the heat exchanger is usually from 70 to 200° C., frequently from 100 to 150° C. Suitable cooling media are air in the case of the corresponding air coolers and cooling liquids, in particular water, in the case of the other cooling apparatuses. Suitable column baffles are in principle all conventional baffles, in particular trays stacked packings and/or dumped packings. Along the trays, bubble trays, sieve trays, valve trays and/or dual-flow trays are preferred. Typically, the total number of trays in the case of a tray column is from 20 to 80 (up to 100 where the quench with dilute acid solution has been integrated into the column), preferably from 50 to 80 (or 100). The crude acrylic acid removed in the side take-off as a rule still contains from 0.1 to 2% by weight of acetic acid, from 0.5 to 5% by weight of water, from 0.05 to 1% by weight of low molecular weight aldehydes, from 0.001 to 1% by weight og maleic acid and/or its anhydride and from 1 to 500 ppm by weight of polymerization inhibitor, based in each case on the weight of crude acrylic acid. The temperature in the bottom of the column is typically from 90 to 130° C., whereas the top temperature is usually from 40 to 80° C., frequently from 50 to 70° C. The temperature at which the crude acrylic acid is removed is in general from 80 to 110° C. The recycle temperature of the high boilers at the entrance into the column is typically from 95 to 115° C. The temperature of the dilute acid solution on recycling into the column is as a rule from 25 to 35° C. In principle, the quench system 2 can be designed in the same way as the quench system 1. According to the invention, the removal of the crude acrylic acid can of course also be carried out via a plurality of collecting trays following after the other at short distances.

According to the invention, the crude acrylic acid removed as a medium-boiler fraction can be fed to, for example, a crystallization for further purification. As a rule no solvent is added, particular no organic solvent. The crystallization method to be used is not subject to any restriction. The crystallization can be carried out continuously or batchwise, in one or more stages, up to virtually any desired purities. If required, water may be added to the crude acrylic acid to be purified by crystallization before a crystallization (up to 10% by weight or more, preferably up to 5% by weight, based on the amount of acrylic acid present). Such an addition facilitates the separation of acetic acid contained as a by-product in the crude acrylic acid, since, in the presence of water, said acetic acid is incorporated to a relatively small extent into the acrylic acid crystals. Moreover, the presence of water reduces the tendency to encrustations.

It is surprising that a crude acrylic acid suitable for esterification can be obtained by only a single crystallization stage. Expediently, this crystallization stage is in the form of a suspension crystallization. A crystallizer advantageous for this purpose is a trough in which wiped cooling plates (through the interior of which a coolant flows) are arranged suspended one behind the other. By wiping the cooling plates, the layer crystallization is suppressed. The crude acrylic acid is passed (pumped or fed with overflow control) continuously through the crystallizer from back to front. The one-phase crude acrylic acid thickens to give a two-phase suspension containing acrylic acid crystals as the solid phase. A crystallizer particularly suitable in this respect is a crystallizer from GMF Gouda (The Netherlands) of the cooling disk crystallizer type. Expediently, the crystals formed are isolated from the abovementioned suspension by means of a centrifuge (for example one from Siebtechnik, of the SHS reciprocating centrifuge type with conical filter drum) and, if required, washed with further-purified crude acrylic acid and/or subjected to sweating as described below. The isolation and washing of the suspension crystals can, however, also advantageously be carried out in a scrubber column, as described, for example, in EP-A 97405, U.S. Pat. No. 3,872,009, EP-A 98637, EP-A 305316, EP-A 105524 and WO 84/00118. The crystals are then usually introduced into a container which advantageously already contains an amount of molten acrylic acid crystals purified in a corresponding manner. If required, this molten acrylic acid additionally contains added polymerization inhibitor (MEHQ, PTZ or 4-hydroxy-TEMPO). As a rule, however, the inhibitor residue remaining in the crystals is sufficient for ensuring adequate inhibition. The acrylic acid crystals obtained are then melted by indirect heating. The acrylic acid melt thus obtainable usually has a purity of ≧98% by weight and can be marketed directly as acrylic acid suitable for esterification.

Instead of a suspension crystallization, a layer crystallization, for example, a falling-film crystallization, may also be used as described in EP-A 616 998 for obtaining pure acrylic acid. For example, water/methanol, water/ethanol and water/ethylene glycol mixtures are suitable as liquid cooling/heating media.

To obtain particularly high purities (pure acrylic acid), the crystallization is expediently carried out as a fractional crystallization. In the case of fractional crystallization, all stages which produce crystals which are purer than the melt fed in are usually referred to as purification stages. All other stages are referred to as the stripping stages. Expediently, multistage processes are operated according to the counter-current principle, in which, after the crystallization in each stage, the crystals are separated from the mother liquor and these crystals are fed to the respective stage having the next highest purity, while the crystallization residue is fed to the respective stage having the next lowest purity.

Advantageously, the temperature of the liquid phase during the crystallization is from +5 to +14° C., in particular from +8° C. to +12° C. The solids content in the crystallizer is advantageously from 0 to 80 g of solid/100 g total mass. In the suspension crystallization, the solids content is preferably from 15 to 35 g of solid/100 g total mass and in the layer crystallization from 50 to 80 g of solid/100 g total mass.

In a possible embodiment of the invention, crystallization is carried out by cooling apparatus walls and/or by evaporating the solution under reduced pressure. In the crystallization by cooling, the heat is removed by means of scraped-surface heat exchangers which are connected to a stirred kettle or to a container without a stirrer. Here, the circulation of the crystal suspension is ensured by a pump. It is also possible to remote the heat via the wall of the stirred kettle having a stirrer passing close to the wall. A further embodiment in the case of the crystallization by cooling is the use of cooling disk crystallizers, as produced, for example, by Gouda (The Netherlands). In a further suitable variant of the crystallization by cooling, the heat is removed by means of conventional heat exchangers (preferably tube-bundle or plate-type heat exchangers). In contrast to scraped-surface heat exchangers, stirred kettles having stirrers passing close to the wall or cooling disk crystallizers, these apparatuses have no device for avoiding crystal layers on the heat-transferring surfaces. If, during operation, the state in which the heat transmission resistance assumes too high a value owing to crystal layer formation is reached, the system switches to a second apparatus. During the operating time of the second apparatus, the first apparatus is regenerated (preferably by melting off the crystal layer or flushing the apparatus with molten crystals). When too high a heat transmission resistance is reached in the second apparatus, the system switches back to the first apparatus, etc. This variant can also be operated cyclically with more than two apparatuses. Moreover, the crystallization can be effected by conventional evaporation of the solution under reduced pressure. In a further embodiment of the invention, the crystallization is carried out in apparatuses in which the crystals grow on cooled surfaces in the crystallization apparatus, i.e. fixed in the apparatus (e.g. the layer crystallization method (cf. for example EP-A 616998) of Sulzer Chemtech (Switzerland) or static crystallization methods (cf. for example FR-A 2668946) of BEFS PROKEM (France)). The acrylic acid crystals obtained are separated from the remaining mother liquor, as stated above. For the case of the layer crystallization or of the static crystallization, the separation of the crystals from the mother liquor can be effected in the crystallization apparatus itself since the crystals are fixed in the apparatus and the mother liquor can be removed by allowing it to run out of the apparatus. The crystals are removed from the crystallization apparatus by melting the crystals and then allowing the melt to run out. For the case of the suspension crystallization, all known solid-liquid separation methods are suitable. In a preferred embodiment of the invention, the crystals are separated from the mother liquor by filtration and/or centrifuging. Advantageously, prethickening of the suspension, for example by hydrocyclone(s), precedes the filtration or centrifuging. All known centrifuges which operate batchwise or continuously are suitable for the centrifuging. Reciprocating-conveyor centrifuges which can be operated in one or more stages are most advantageously used. Helical-screen centrifuges or helical-conveyor centrifuges (decanters) are also suitable. Filtration is advantageously carried out by means of suction filters, which are operated batchwise or continuously with or without a stirrer, or by means of belt filters. In general, the filtration can be carried out under superatmospheric or reduced pressure.

During and/or after the solid-liquid separation, further process steps for increasing the purity of the crystals or of the crystal cake can be provided. It a particularly advantageous embodiment of the invention, the separation of the crystals from the mother liquor is followed by one-stage or multistage washing and/or sweating of the crystals or of the crystal cake. During washing, the amount of wash liquid is appropriately from 0 to 500, preferably from 30 to 100, g of wash liquid/100 g of crystals. The wash liquid used is not subject to any restriction. Advantageously, however, washing is effected with pure product, i.e. with a liquid which contains acrylic acid whose purity is the same as or higher than that of the crystal cake to be washed. Washing with water is also possible. The washing can be carried out in apparatuses usual for this purpose.

Advantageously, scrubber columns (for example those having mechanical bed transport (for example from Niro Process Technology B.V., in s'Hertogenbusch (NL)) or those with hydraulic bed transport (for example from TNO in Apeldoorn (NL)), in which the separation of the mother liquor and the washing are carried out in one apparatus or centrifuges which can be operated in one or more stages or suction filters or belt filters are used. The washing can be carried out on centrifuges or belt filters in one or more stages. Here, the wash liquid can be fed countercurrent to the crystal cake.

Sweating involves local melting of contaminated regions. Advantageously, the amount of sweating is from 0 to 80 g, preferably from 5 to 35 g, of molten crystals/100 g of crystals prior to sweating. The sweating is particularly preferably carried out on centrifuges or belt filters and in crystallizers in which the crystals are fixed in the crystallizer (for example layer crystallizers). Carrying a combination of washing and sweating in one apparatus may also be suitable.

The acrylic acid crystals after the solid-liquid separation and any further washing and/or sweating represent the purified acid from the process. The purity of the crystals obtained is as a rule from 97 to 99.99% by weight or more, in particular from 98.5 to 99.9% by weight, of acrylic acid. The crystals prepared by the novel process now contain very small amounts of impurities, such as acetic acid, propionic acid, diacrylic acid.

In summary, it may once again be stated that, according to the invention, the crystallization can be realised in principle as a suspension crystallization and/or as a layer crystallization (the crystals which separate out remain fixed in the crystalllizer). For example, falling-film crystallization (for example as described in EP-A 616 998), crystallization in a tube with full flow (for example according to DE-A 2606364) or static crystallization are suitable as the latter crystallization method.

In the suspension crystallization, the cooling can be realised directly (for example evaporation under reduced pressure) and/or indirectly by means of cooled surfaces. Suitable crystallizers for such a suspension crystallization are: stirred kettles having stirrers passing close to the wall, scrapped-surface heat exchangers, cooling disk crystallizers from Gouda and circulation crystallization using heat exchangers without an apparatus for avoiding crystal layer formation.

If desired, the purified acid can be esterified by a known method or further purified by known methods.

To increase the yield of acrylic acid, very generally the mother liquor remaining after the end of the crystallization is recycled, at least in part as described at the outset, into the separation column. According to the invention, the proportion of the recycled mother liquor is from >0 to 100% by weight, preferably from 80 to 100% by weight, based on the amount of said mother liquor obtained. The recycling of the polymerization inhibitor separated off during the crystallization is ensured simultaneously with the recycling of the mother liquor. The novel process ensures completely satisfactory inhibition of polymerization with minimum use of polymerization inhibitors.

According to the invention, molecular oxygen or an inert gas stream containing molecular oxygen can, if required, be passed through the separation column together with the product mixture. This enhances the effect of the added polymerization inhibitors.

Of course, the process for the preparation of methacrylic acid, equivalent to the process described, can be inhibited and operated in a manner corresponding to that described here.

Possible starting compounds for the gas-phase oxidation are isobutene, methyl tert-butyl ether, isobutane, isobutyric acid, tert-butanol, isobutyraldehyde or methacrolein. Otherwise, the statements made in DE-A 19740253 and DE-A 19740252 are applicable in this context.

As described, the inhibition of polymerization in the novel process can also be carried out by adding an aqueous MEHQ solution at the top of the column and adding a solution of PTZ in acrylic acid in the middle part of the column. The quench with dilute acid solution is then likewise stabilized by means aqueous MEHQ solution.

Figure 2:
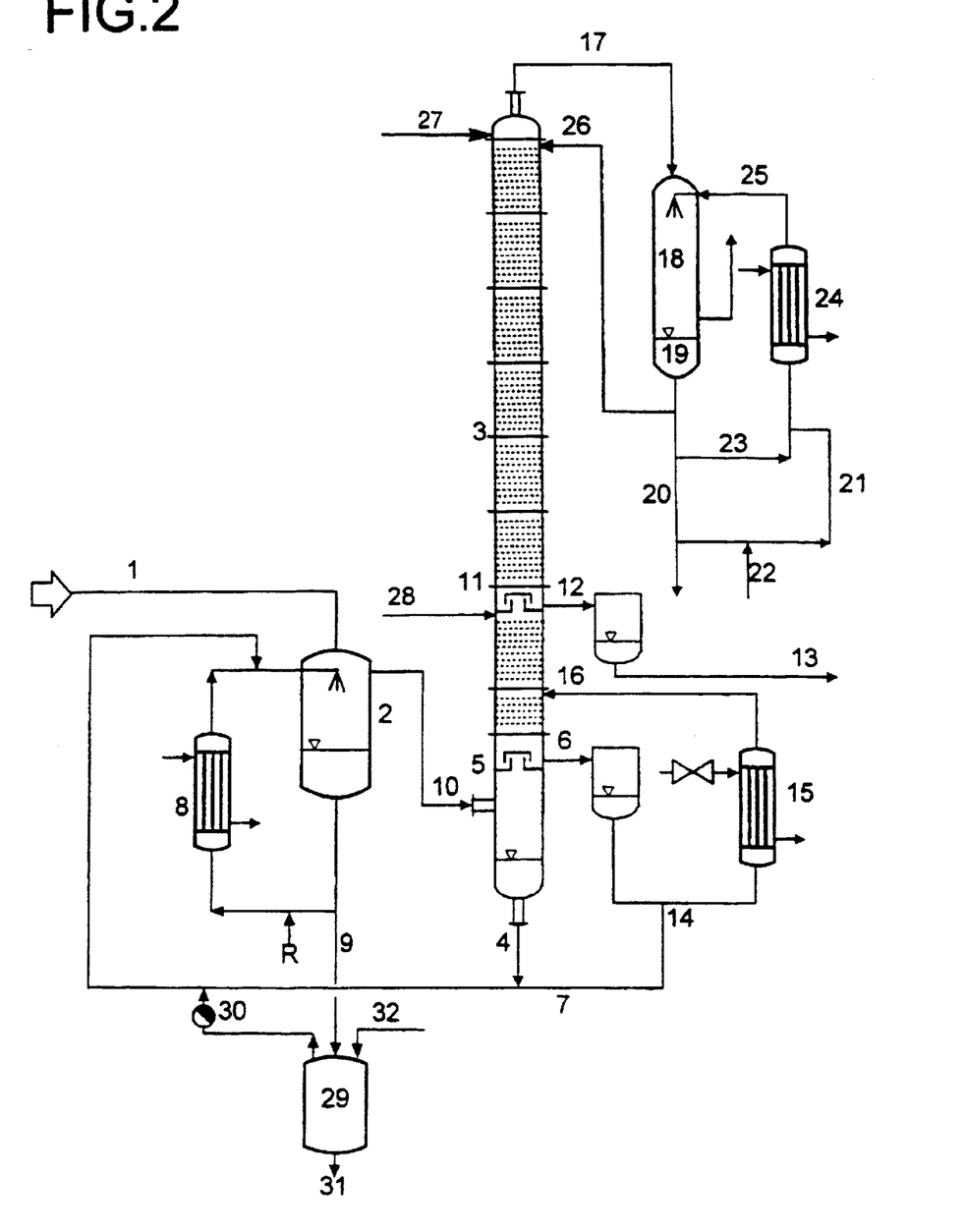
FIG. 2 shows an embodiment of the present invention in which a cleavage of acrylic acid monomers is conducted in the production of acrylic acid by fractional condensation of a product gaseous mixture obtained from the gas phase oxidation of propane or propene.

It is surprising that the novel integration of the cleavage has virtually no adverse affect on the residence time of the working-up process. FIG. 2 shows a schematic diagram of the novel procedure. The comparative example and the examples indicate the meaning of the numbers in FIG. 2.

EXAMPLES

Figure 1:
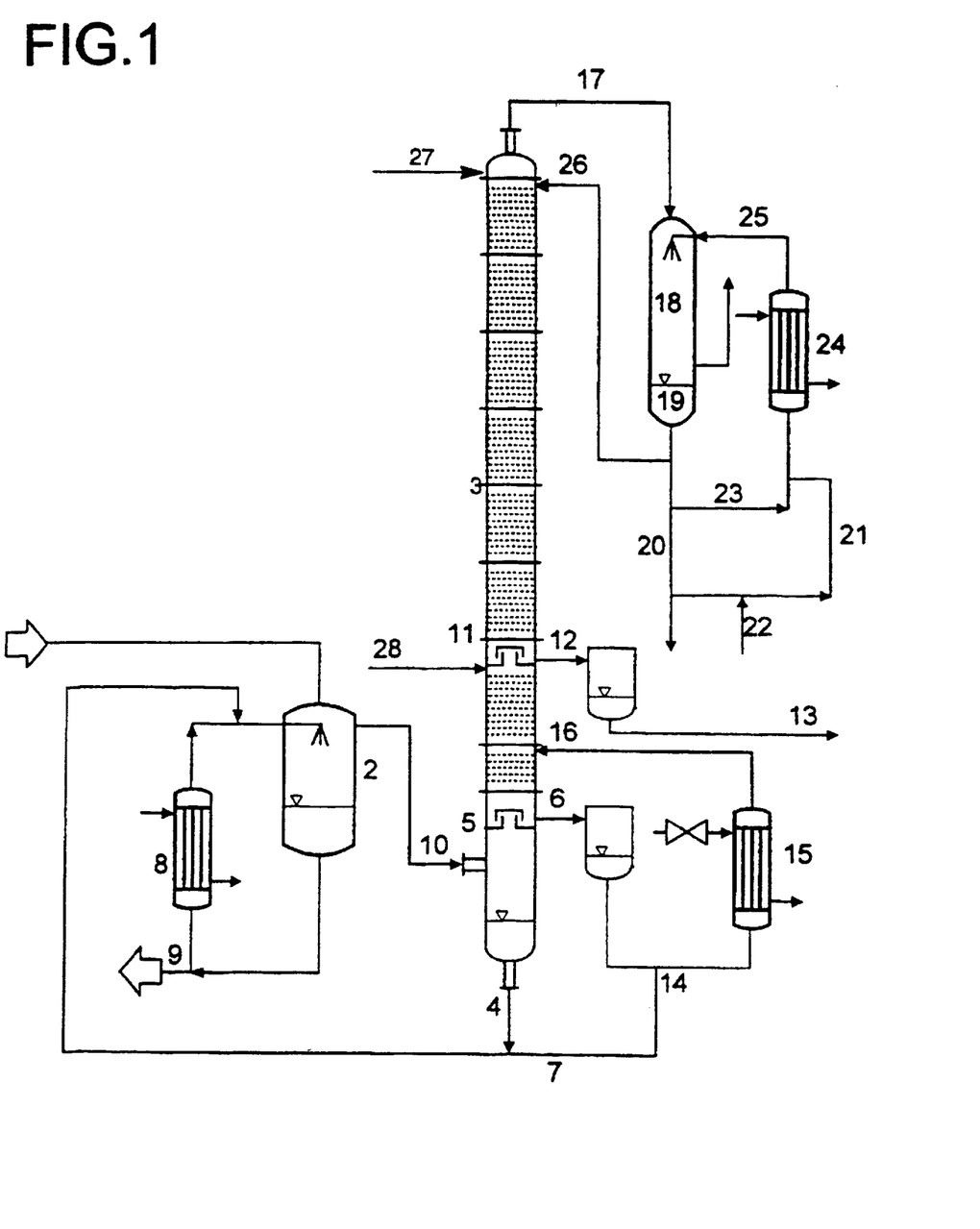
FIG. 1 shows a comparative example of a method of producing acrylic acid by fractional condensation of a product gaseous mixture obtained from the gas phase oxidation of propane or propene.

Comparative Example
(The Reference Symbols Used in this Example Relate to FIG. 1 Attached to this Document)

A product gas mixture (1) having a temperature of 270° C. and the following composition was obtained from a gas-phase oxidation under heterogeneous catalysis:

| | |
|---|---|
| 11.5% by weight | acrylic acid |
| 0.3% by weight | acetic acid |
| 30 ppm by weight | propionic acid |
| 0.09% by weight | maleic anhydride |
| 0.01% by weight | acrolein |
| 0.1% by weight | formaldehyde |
| 30 ppm by weight | furfural |
| 0.001% by weight | benzaldehyde |
| 0.3% by weight | propene |
| 3.4% by weight | oxygen |
| 5.3% by weight | water |
| 1.7% by weight | carbon oxides, the remaining amount comprising $N_2$ |

The product gas mixture (3600 g/h) was cooled to 136° C. in a spray cooler (2). 750 g/h (7) of a total of 7000 g/h of high-boiler fraction (6) removed from the separation column (3) via the collecting trays (5) (having a temperature of 100° C.) were used as spray liquid (quench liquid 1) (bottom liquid 4 did not occur). The spray liquid was circulated via the tube-bundle heat exchanger (8) operated with thermal oil. 40 g/h of the quench liquid 1 were removed continuously from the circulation as a purge.

The product gas mixture cooled to 136° C. was fed (10) to the separation column below the collecting tray (5).

The column was a tray column having 25 dual-flow and 50 bubble trays (one bubble cap per tray). The tray diameter was 49 mm. The dual-flow trays had six holes per tray. The hole diameter of the first five dual-flow trays was 9.5 mm. The subsequent ten trays had a hole diameter of 9 mm and the hole diameter of the last 5 dual-flow trays was 8.7 mm. The tray above tray 15 was in the form of a further collecting tray (11). 1800 g/h of a crude acrylic acid (12) having a temperature of 97° C. and containing

| | |
|---|---|
| acrylic acid | 97.3% by weight |
| acetic acid | 0.8% by weight |
| propionic acid | 600 ppm by weight |
| furfural | 700 ppm by weight |
| maleic acid anhydride | 40 ppm by weight |
| benzaldehyde | 200 ppm by weight |
| water | 1.3% by weight | were taken off via said collecting tray and fed to a suspension crystallizer (13). A part (6250 g/h) of the high-boiler fraction (14) removed was heated to 105° C. in a tube-bundle heat exchanger operated with thermal oil and was recycled (16) to the column at the fifth tray.

The crystallizer was a stirred container (3 l internal volume) having a helical ribbon impeller. The heat of crystallization was removed via the double jacket of the container. The equilibrium temperature of the solution was 9.7° C. The suspension produced during the crystallization (solids content about 25% by weight) was separated batchwise into crystals and mother liquor on a centrifuge at 2000 rpm centrifuge diameter 300 mm) and over a centrifuging time of 3 min. The crystals were then washed with molten (previously washed) crystals (80 g) for 20 seconds at 2000 rpm. The mother liquor together with the wash liquid was recycled (28) to the separation column at the 15th tray.

The analysis of the molten pure crystals (370 g/h) gave the following contents:

| | |
|---|---|
| acrylic acid | 99.5% by weight |
| acetic acid | 0.3% by weight |
| propionic acid | 200 ppm by weight |
| maleic anhydride | 20 ppm by weight |
| furfural | 20 ppm by weight |
| benzaldehyde | 5 ppm by weight |
| water | 0.06% by weight |

A gaseous mixture (17) was removed from the top of the column and subjected to a partial condensation in the spray cooler (18). 480 g/h of the resulting dilute acid solution were recycled (26) to the top of the column at a temperature of 30° C. 220 g/h of the dilute acid solution were removed continuously. 90 g/h of the removed dilute acid solution were mixed with MEHQ (22) and, in the form of 0.5% strength by weight aqueous stabilizer solution (21), together with the remaining amount of the dilute acid solution (23), cooled to 18° C. by means of the water-cooled tube-bundle heat exchanger (24), were used as spray liquid (25). Using another part of the removed dilute acid solution (alternatively, a corresponding amount of fresh water can also be used here), a 0.5% strength aqueous solution of 4-hydroxy-TEMPO was prepared and was fed (27) at a temperature of 20 to 30° C. to the 75th tray of the separation column in an amount of 18 g/h.

The separation apparatus described was operated for 40 days without significant polymer formation.

Example 1

In a heatable stirred reactor (double jacket) having an internal volume of 1 l, 800 g of the purged quench liquid 1 from the comparative example were mixed with 1% by weight of $Na_2CO_3$ (based on the weight of the purge) and heated to 180° C. at 300 mbar. The cleavage products were separated off continuously in gaseous form via a column filled with Raschig rings (5 mm) (height of fill: 30 cm) and condensed without the addition of polymerization inhibitors. 730 g of cleavage product were condensed in the course of 3.5 hours. This corresponds to a recovery rate of about 90% by weight. According to the gas chromatographic analysis the condensate also comprised diacrylic acid (about 1% by weight), 0.15% by weight of benzaldehyde and about 0.08% by weight of furfural, apart from acrylic acid and inhibitor.

Example 2

The procedure was as in Example 1, except that, instead of 1% by weight of $Na_2CO_3$, 1% by weight of dodecylbenzenesulfonic acid was used as the cleavage catalyst. 495 g of cleavage product having a composition similar to that in Example 1 were condensed in the course of 4.75 hours. This corresponds to a recovery rate of about 61% by weight.

Example 3

A circulation reactor (29) consisting of glass and heated by means of a heating element was filled with 250 g of the purged quench liquid 1 from the comparative example and was heated. In addition to the 4-OH-TEMPO contained in the 250 g of purged quench liquid 1, 2000 ppm by weight of phenothiazine were added for costabilization. The cleavage temperature was 182° C. and the cleavage pressure 500 mbar. No cleavage catalyst was added (32). 155 g/h of purged quench liquid 1 (9) were fed under level control to the circulation reactor filled in the manner described. The cleavage products were separated off in vapor form via a splash guard mounted on the reactor and were condensed (30) in an amount of 113 g/h (this corresponds to a recovery rate of 73% by weight) without addition of polymerization inhibitor. The condensate consisted of about 3.2% by weight of diacrylic acid, 0.06% by weight of benzaldehyde, 0.3% by weight of acetic acid and 0.03% by weight of propionic acid in addition to acrylic acid and inhibitor. 40 g/h of cleavage residue were removed continuously (31) from the cleavage reactor and disposed off.

Example 4

As in the case of the comparative example, except that 30 g/h of the cleavage condensate cooled to 100° C. and obtained from Example 3 were also added to the spray liquid (the addition point was shortly before the spray nozzle). In a corresponding manner, the amount of pure crystals obtained was about 400 g/h.

Within 40 days of operation of the separation apparatus described, the recycling of the cleavage condensate had no visible effect on the polymer formation. The point marked by R in FIG. 2 is also suitable as an alternative addition point for the cleavage condensate.

We claim:

1. A process for the preparation of acrylic acid, comprising:

partially oxidizing propane, propene, acrolein or a mixture of propene and acrolein in the gas phase with molecular oxygen over a solid heterogeneous catalyst at elevated temperature thereby producing an acrylic acid containing hot product gas mixture;

reducing the temperature of said hot product gas mixture by direct cooling by means of a quench liquid 1 which produces an unvaporized portion of quench liquid 1 which is circulated via a heat exchanger which provides indirect cooling, if necessary, and a portion of the unvaporized quench liquid 1 being removed as a purge from the circulation of quench liquid 1;

passing the cooled product gas mixture obtained to a column equipped with baffles which have separation ability where the gas ascends the column and the gas mixture is fractionally condensed into a crude acrylic acid which is removed at a side take-off of the column and (i) a bottom liquid containing acrylic acid oligomers which is removed from the bottom of the column, or (ii) a high boiler fraction which is removed from a side take-off of the column in the vicinity of the bottom or (iii) a mixture of a bottom liquid containing acrylic acid oligomers which is removed from the bottom of the column and a high boiler fraction which is removed from a side take-off of the colunm in the vicinity of the bottom, wherein (i), (ii) or (iii) is used as the quench liquid 1;

feeding said purged quench liquid 1 to a cleavage vessel;

cleaving acrylic acid oligomers in the purged quenched liquid 1 at elevated temperature into acrylic acid which has escaped in gaseous form from the liquid phase; and condensing the acrylic acid vapor and feeding the resulting condensate into circulation in the process system as quench liquid 1.

2. The process as claimed in claim 1, wherein the temperature of said crude acrylic acid removed from the column is 80 to 110° C and wherein the high boilers are recycled into the column at a temperature of 95 to 115° C.

3. The process as claimed in claim 2, wherein the inorganic salt is at least one salt selected from the group consisting of NaOH, $Na_2CO_3$, $NaHCO_3$, KOH, $K_2CO_3$, $KHCO_3$, LiOH, $Li_2CO_3$ and $CaCO_3$.

4. The process as claimed in claim 1, wherein the cleavage is conducted at a temperature ranging from 130 to 250° C.

5. The process as claimed in claim 1, wherein the cleavage is conducted at a pressure ranging from 25 to 600 mbar.

6. The process as claimed in claim 1, wherein 4-OH-TEMPO is present as a polymerization inhibitor inside the column in which the fractional condensation occurs.

7. The process as claimed in claim 1, wherein said hot product gas mixture has the composition:

from 1 to 30% by weight of acrylic acid, from 0.01 to 3% by weight of acetic acid, from 0.01 to 1% by weight of propionic acid, from 0.01 to 0.5% by weight of maleic acid/maleic anhydride, from 0.05 to 1% by weight of acrolein,
from 0.05 to 1% by weight of formaldehyde,
from 0.1 to 1% by weight of furfural,
from 0.01 to 0.5% by weight of benzaldehyde,
from 0.01 to 1% by weight of propene,
from 0.05 to 10% by weight of oxygen,
from 1 to 30% by weight of water, and the remainder inert gases, carbon oxides, methane and propane.

8. The process as claimed in claim 1, wherein said crude acrylic acid removed by way of the side take-off, besides acrylic acid, comprises:

from 0.1 to 2% by weight of acetic acid,
from 0.5 to 5% by weight of water,
from 0.05 to 1% by weight of low molecular weight aldehydes,
from 0.001 to 1% by weight of maleic acid, maleic anhydride or combinations thereof, and
from 1 to 500 ppm of polymerization inhibitor.

9. The process as claimed in claim 1, wherein the temperature at the bottom of said column ranges from 40 to 80° C.

10. The process as claimed in claim 1, wherein the temperature of said crude acrylic acid removed from the column is 80 to 110° C and wherein the high boilers are recycled into the column at a temperature of 95 to 115° C.

11. The process as claimed in claim 1, wherein said crude acrylic acid which is removed from the column has a purity $\geq$95% by weight.

12. The process as claimed in claim 1, comprising purifying said crude acrylic acid by distillation, crystallization or a combination thereof and recycling a portion of the bottom liquids and mother liquors obtained from the distillation and crystallization operations to the column.

* * * * *